United States Patent [19]
Turturro et al.

[11] Patent Number: 5,967,997
[45] Date of Patent: Oct. 19, 1999

[54] ENDOSCOPIC SURGICAL INSTRUMENT WITH DEFLECTABLE AND ROTATABLE DISTAL END

[75] Inventors: Vincent Turturro, Miramar; Sergio Rodriguez, Hialeah, both of Fla.

[73] Assignee: Symbiosis Corporation, Miami, Fla.

[21] Appl. No.: 09/069,763

[22] Filed: Apr. 30, 1998

[51] Int. Cl.[6] .................................................. A61B 5/00
[52] U.S. Cl. ........................................ 600/567; 606/170
[58] Field of Search .......................... 600/562, 564–567, 600/585; 606/205, 167, 170

[56] References Cited

U.S. PATENT DOCUMENTS

| | | | |
|---|---|---|---|
| 4,499,895 | 2/1985 | Takayama | 128/6 |
| 4,503,842 | 3/1985 | Takayama | 128/4 |
| 4,559,928 | 12/1985 | Takayama | 128/6 |
| 4,770,443 | 9/1988 | Yamamoto | 285/39 |
| 4,880,015 | 11/1989 | Nierman | 128/751 |
| 4,887,612 | 12/1989 | Esser et al. | 128/751 |
| 4,945,920 | 8/1990 | Clossick | 128/751 |
| 4,991,957 | 2/1991 | Sakamoto et al. | 356/241 |
| 5,183,470 | 2/1993 | Wettermann | 604/281 |
| 5,209,747 | 5/1993 | Knoepfler | 606/16 |
| 5,231,989 | 8/1993 | Middleman et al. | 128/657 |
| 5,251,611 | 10/1993 | Zehel et al. | 128/4 |
| 5,254,130 | 10/1993 | Poncet et al. | 606/206 |
| 5,275,608 | 1/1994 | Forman et al. | 606/170 |
| 5,318,528 | 6/1994 | Heaven et al. | 604/95 |
| 5,330,502 | 7/1994 | Hassler et al. | 606/205 |
| 5,336,221 | 8/1994 | Anderson | 606/27 |
| 5,345,937 | 9/1994 | Middleman et al. | 128/657 |
| 5,354,311 | 10/1994 | Kambin et al. | 606/205 |
| 5,372,587 | 12/1994 | Hammerslag et al. | 604/95 |
| 5,374,277 | 12/1994 | Hassler | 606/207 |
| 5,378,234 | 1/1995 | Hammerslag et al. | 604/95 |
| 5,383,849 | 1/1995 | Johlin, Jr. | 604/53 |
| 5,383,888 | 1/1995 | Zvenyatsky et al. | 606/206 |
| 5,391,180 | 2/1995 | Tovey et al. | 606/205 |
| 5,403,342 | 4/1995 | Tovey et al. | 606/205 |
| 5,409,453 | 4/1995 | Lundquist et al. | 604/22 |
| 5,467,763 | 11/1995 | McMahon et al. | 600/201 |
| 5,474,581 | 12/1995 | Lang | 606/205 |
| 5,489,270 | 2/1996 | van Erp | 604/95 |
| 5,490,819 | 2/1996 | Nicholas et al. | 600/201 |
| 5,501,654 | 3/1996 | Failla et al. | 600/204 |
| 5,514,157 | 5/1996 | Nicholas et al. | 606/206 |
| 5,520,678 | 5/1996 | Heckele et al. | 606/1 |
| 5,542,432 | 8/1996 | Slater et al. | 128/751 |
| 5,545,148 | 8/1996 | Wurster | 604/223 |
| 5,571,136 | 11/1996 | Weaver | 606/205 |
| 5,607,450 | 3/1997 | Zenyatsky et al. | 606/206 |
| 5,609,601 | 3/1997 | Kolesa et al. | 606/170 |
| 5,620,415 | 4/1997 | Lucey et al. | 604/22 |
| 5,628,778 | 5/1997 | Kruse et al. | 607/123 |
| 5,643,294 | 7/1997 | Tovey et al. | 606/148 |
| 5,645,075 | 7/1997 | Palmer et al. | 128/749 |
| 5,645,957 | 7/1997 | Levin | 606/207 |
| 5,715,817 | 2/1998 | Stevens-Wright et al. | 128/642 |

FOREIGN PATENT DOCUMENTS 9-168540  6/1997  Japan.

*Primary Examiner*—Max Hindenburg
*Attorney, Agent, or Firm*—Finnegan, Henderson, Farabow, Garrett & Dunner, L.L.P.

[57] ABSTRACT

An endoscopic bioptome having a proximal end and a distal end includes a proximal handle assembly including first and second actuators, a distal end effector assembly having jaws for cutting tissue samples, and a hollow member extending between the handle and the end effector assembly. The hollow member includes a first axial portion extending from the proximal end to a second axial portion at the distal end of the hollow member. The second axial portion is more flexible than the first axial portion. The bioptome further includes a control member connected at the proximal end to the handle assembly and at the distal end to the end effector assembly. Actuation of the first actuator causes the control member to open and close the jaws. The bioptome further includes a deflecting device connected at the proximal end to the second actuator and extending through at least a portion of the hollow member. Actuation of the second actuator causes the deflecting device to axially displace into the second axial portion to deflect the distal end of the hollow member.

26 Claims, 8 Drawing Sheets

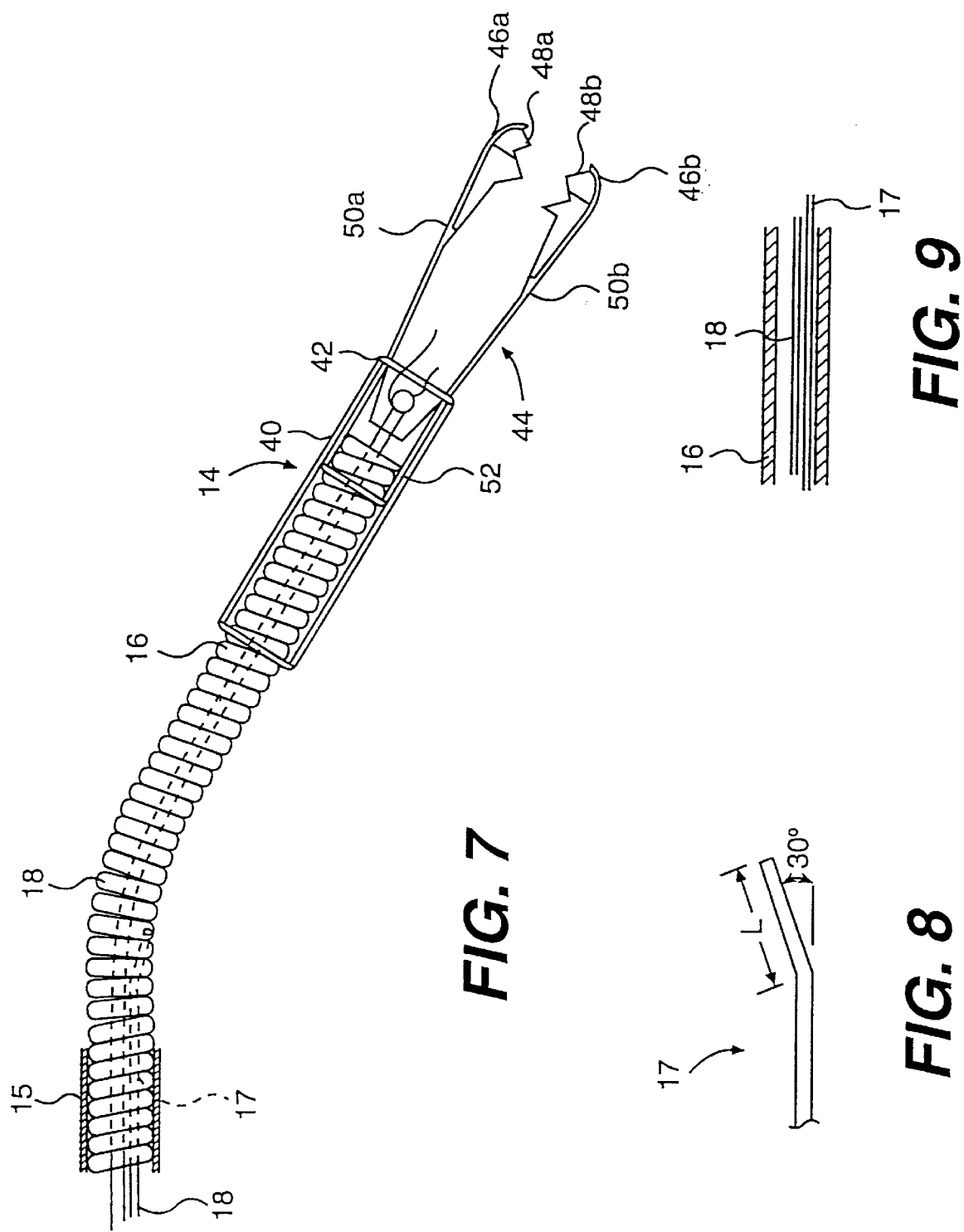

ENDOSCOPIC SURGICAL INSTRUMENT WITH DEFLECTABLE AND ROTATABLE DISTAL END

BACKGROUND OF THE INVENTION

1. Field of the Invention

The present invention relates to endoscopic surgical instruments. More particularly, this invention relates to an endoscopic instrument, such as a biopsy forceps device, that deflects and rotates at the distal end.

2. Background of the Related Art

An endoscopic surgical procedure is typically performed with an endoscope and an endoscopic surgical instrument within the endoscope. The endoscope is a long flexible tube carrying fiber optics for viewing, for example, biopsy sites. A common endoscopic procedure entails the taking of biopsy tissue samples with a biopsy device called a bioptome. The bioptome inserts into a narrow lumen in the endoscope. The bioptome typically includes a long flexible coil having a pair of opposed jaws at a distal end and a manual actuator at the proximal end. Manipulation of the actuator opens and closes the jaws.

During a biopsy tissue sample procedure, the surgeon guides the endoscope to a biopsy site while viewing the biopsy site through the fiber optics. The bioptome is inserted through the narrow lumen of the endoscope until the opposed jaws arrive at the biopsy site. While viewing the biopsy site through the fiber optics of the endoscope, the surgeon positions the jaws around the tissue to be sampled and manipulates the actuator so that the jaws close around the tissue. A sample of the tissue is then cut or torn away from the biopsy site while it is trapped between the jaws of the bioptome. Keeping the jaws closed, the surgeon withdrawals the bioptome from the endoscope and then opens the jaws to collect the biopsy tissue sample.

A biopsy tissue sampling procedure often requires the taking of several tissue samples either from the same or different biopsy sites. Most bioptomes are limited to taking a single tissue sample, after which the device must be withdrawn from the endoscope and the tissue collected before the device can be used again to take a second tissue sample. Multiple sample bioptomes, however, have been devised to take multiple tissue samples prior to withdrawal from the endoscope. Many multiple and single sample bioptomes are unable to take tangential biopsies, i.e. tissue located laterally from the jaws of the bioptome, or can take tangential biopsies only through excessive manipulation of the endoscope, causing trauma to the patient.

SUMMARY OF THE INVENTION

It is therefore as object of the invention to provide a bioptome capable of taking tangential tissue samples.

It is further object of the invention to provide an endoscopic surgical instrument that deflects and rotates at the distal end to reach tangential tissue sites.

It is a still further object of the invention to provide an endoscopic bioptome that is easy to manufacture and has a low manufacturing cost.

It is another object of the invention to provide such an endoscopic bioptome that is easy to use.

Additional objects and advantages of the invention will be set forth in part in the description which follows, and in part will be obvious from the description, or may be learned by practice of the invention. The objects and advantages of the invention will be realize and attained by means of the elements and combinations particularly pointed out in the appended claims.

To achieve the objects and in accordance with the purpose of the invention, as embodied and broadly described herein, the invention includes an endoscopic bioptome having a proximal end and a distal end. The bioptome includes a proximal handle assembly including first and second actuators, a distal end effector assembly having jaws for cutting tissue samples, and a hollow member extending between the handle and the end effector assembly. The hollow member includes a first axial portion extending from the proximal end to a second axial portion at the distal end of the hollow member. The second axial portion is more flexible than the first axial portion. The bioptome further includes a control member connected at the proximal end to the handle assembly and at the distal end to the end effector assembly. Actuation of the first actuator causes the control member to open and close the jaws. The bioptome further includes a deflecting device connected at the proximal end to the second actuator and extending through at least a portion of the hollow member. Actuation of the second actuator causes the deflecting device to axially displace into the second axial portion to deflect the distal end of the hollow member.

According to another aspect, the invention includes an endoscopic surgical instrument having a proximal end and a distal end. The instrument includes a proximal manual actuator including first and second actuators, a distal end effector assembly for performing a surgical operation, and a hollow member extending between the manual actuator and the end effector assembly. The hollow member includes a first axial portion extending from the proximal end to a second axial portion at the distal end of the flexible member. The second axial portion is more flexible then the first axial portion. The instrument further includes a control member connected at the proximal end to the manual actuator and at the distal end to the end effector assembly so that actuation of the first actuator causes the distal end effector to perform the surgical operation. The instrument further includes a deflecting device connected at the proximal end to the second actuator and extending along the flexible member. Actuation of the second actuator causes the deflecting device to axially displace into the second axial portion to deflect the distal end of the flexible member.

According to yet another aspect, the invention includes an endoscopic bioptome having a proximal end and a distal end. The bioptome comprises a proximal handle assembly including at least one actuator, a distal end effector assembly having jaws for cutting tissue samples, and a hollow member extending between the handle and the end effector assembly. The hollow member includes a first axial portion extending substantially the entire length of the hollow member from the proximal end and a second axial portion at the distal end of the hollow member. The bioptome further includes a control member extending through the hollow member and connected at the proximal end to the handle and at the distal end to the end effector assembly. Actuation of the at least one actuator causes the control member to open and close the jaws. The bioptome further includes a deflecting device connected at the proximal end to the at least one actuator and extending through the first axial portion of the hollow member. The first axial portion has a first stiffness so that a distal end of the deflecting device remains substantially straight when the distal end of the deflecting device is contained within the first axial portion, and the second axial portion has a second stiffness so that the distal end of the deflecting device bends when the distal end of the deflecting device is contained within the second axial portion.

It is to be understood that both the foregoing general description and the following detailed description are exemplary and explanatory and are not restrictive of the invention, as claimed.

BRIEF DESCRIPTION OF THE DRAWINGS

The accompanying drawings, which are incorporated in and constitute a part of this specification, illustrate an embodiment of the invention and together with the description, serve to explain the principles of the invention. In the drawings.

FIG. 7 is a side elevation view in partial section of the bioptome shown in FIG. 6 and rotated at the distal end according to a preferred embodiment of the present invention;

FIG. 8 is a side elevation view of the distal portion of a deflecting wire for use in the bioptome shown in FIGS. 1–7 according to a preferred embodiment of the present invention;

FIG. 9 is a cross-sectional side elevation view of a coil for use in a bioptome according to a preferred embodiment of the present invention.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

The present invention is directed towards an endoscopic bioptome capable of taking tangential biopsies, i.e. biopsies located laterally from the jaws at the distal end of the bioptome. The bioptome described in detail below includes a deflecting device within the long flexible coil of the bioptome. The surgeon manipulates an actuator at the proximal end of the bioptome to cause the deflecting device to deflect and/or rotate the distal end of the bioptome. This enables the jaws to reach and take tangential biopsy samples.

The deflecting device is described below and shown in the figures in connection with a multiple sample bioptome. The invention described herein, however, is fully capable of being incorporated into all endoscopic bioptomes, including those taking single tissue samples. Even further, the deflectable and rotatable distal end described herein is capable of being incorporated into various endoscopic surgical instruments, including biliary biopsy forceps and snares, that require the deflection and/or rotation of the end effector to reach tangential tissue sites.

Figure 1:
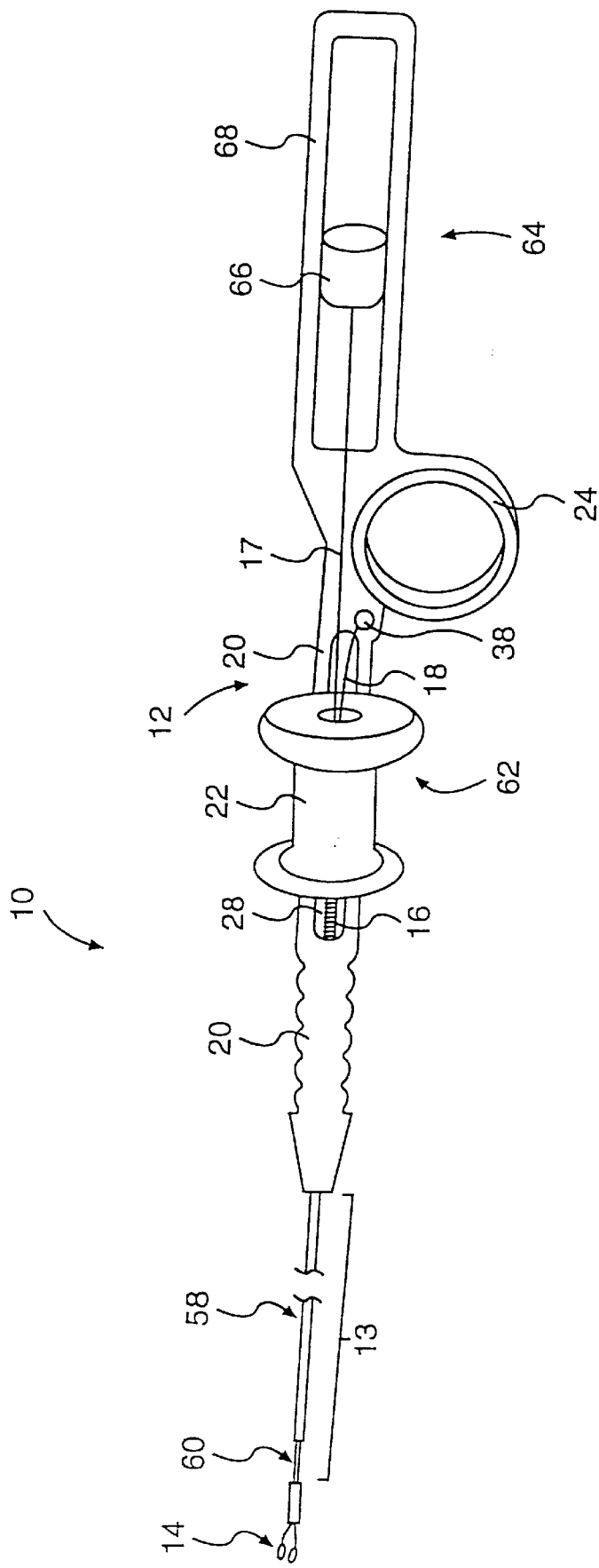
FIG. 1 is a side elevation view of a preferred embodiment of an endoscopic bioptome according to the present invention.

FIG. 1 shows an endoscopic bioptome 10 according to the present invention. Bioptome 10 includes three main components: a handle 12 at the proximal end of bioptome 10; an end effector 14 at the distal end of bioptome 10; and a long tube-like section 13 that connects handle 12 to end effector 14. Section 13 includes a long first axial portion 58 and a relatively short second axial portion 60 to be described later.

Figure 3:
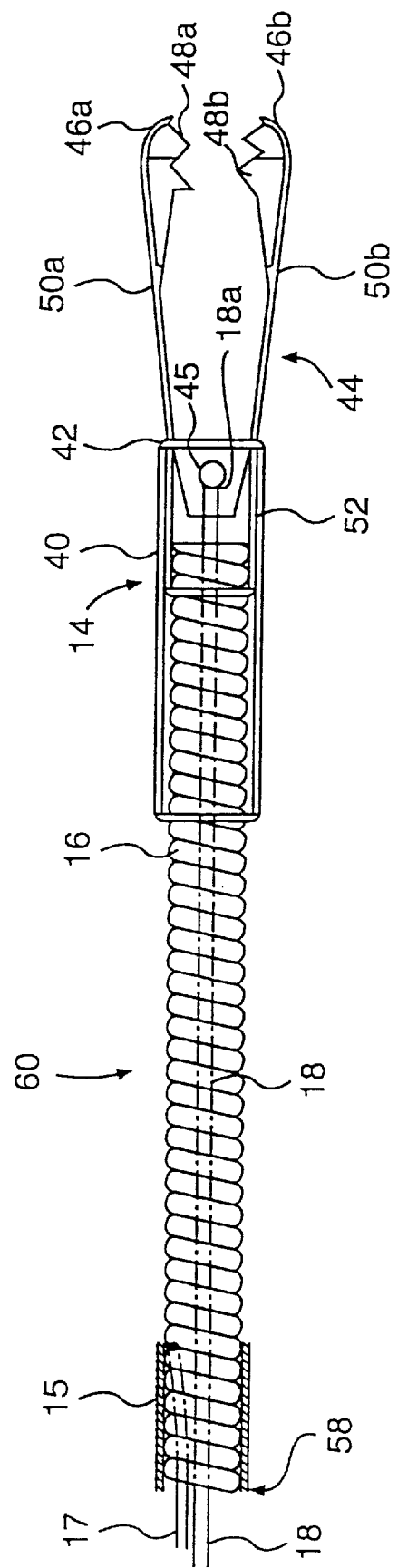
FIG. 3 is a side elevation view in partial section of the distal end of the bioptome shown in FIG. 1 according to a preferred embodiment of to the present invention.

FIG. 3 shows the distal end of bioptome 10, including end effector 14 and the distal end of section 13. Section 13 includes a long, flexible, and hollow coil 16 and a control wire 18 extending therethrough. Coil 16 and wire 18 couple handle 12 to end effector 14. A deflecting device, shown as a deflecting wire 17, also extends through at least a portion of coil 16 and terminates at the distal end of bioptome 10.

An outer sleeve 15 surrounds and covers substantially the entire length of coil 16. The length of coil covered by sleeve 15 corresponds to first axial portion 58 of section 13. First axial portion 58 extends substantially the entire length of coil 16 from proximal handle 12 to the proximal end of second axial portion 60. Second axial portion 60 extends along coil 16 from the distal end of sleeve 15 to end effector 14. Sleeve 15 does not cover second axial portion 60. Second axial portion 60 preferably has a length of approximately 0.75 inch.

As shown in FIG. 9, coil 16 is preferably a flat wire coil approximately 0.008" thick and 0.020" wide and made of stainless steel or other suitable material that is highly flexible. The flat wire coil is wrapped around a mandrel to form coil 16. The use of a flat wire coil, as opposed to a round wire coil, leaves sufficient space within coil 16 for control wire 18 and deflecting wire 17. It is to be understood that other suitable sizes, types, materials, and manufacturing methods for coil 16 to permit sufficient flexibility and space within coil 16 are within the scope of this invention.

Sleeve 15 is preferably formed from heat shrink tubing made of PTFE, FEP, polyolefin, or other suitable material that provides sufficient stiffness to coil 16 yet is flexible enough to allow coil 16 and sleeve 15 to weave through a lumen of an endoscope. Sleeve 15 is preferably applied to coil 16 by heat so that it is integrally connected to coil 16.

The stiffness of sleeve 15 causes first axial portion 58 to be less flexible than second axial portion 60. The portion of coil 16 that comprising second axial portion 60 may be slightly stretched to remove a certain amount of preload of coil 16 and thereby further increase the flexibility of second axial portion 60. As will be described, the relative difference in flexibility between first axial portion 58 and second axial portion 60 permits the distal portion of bioptome 10 to deflect and rotate.

Figure 10B:
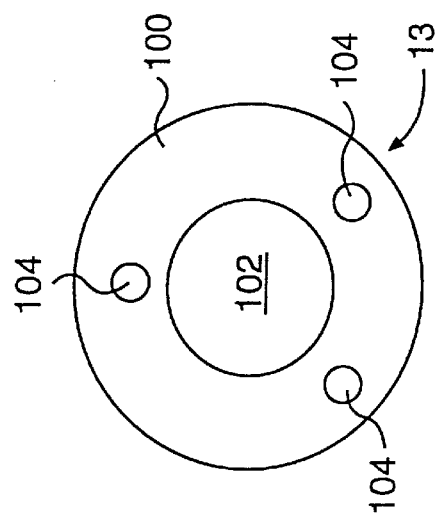
FIG. 10a–10c are cross-sectional views of a flexible extruded section for use in a bioptome according to another preferred embodiment of the present invention.
Figure 10C:
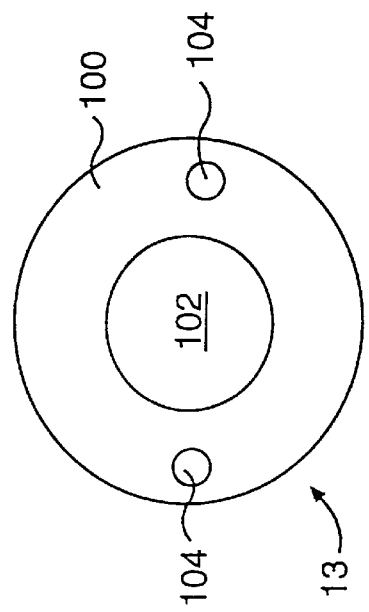
Figure 10A:
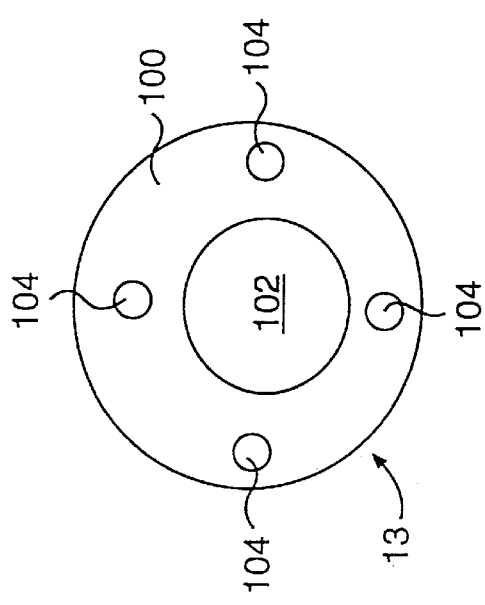

As an alternative to the construction of section 13 including coil 16 and sleeve 15 described above, hollow tube-like section 13 may be constructed of an extrusion that has variable stiffness along its length. In this manner, the majority of section 13, for example first axial portion 58, is stiff relative to the more flexible distal end corresponding, for example, to second axial portion 60. As a further alternative, section 13 may be constructed of a rigid coil with a flexible extrusion attached to the distal end. As yet another alternative, section 13 may include a plastic extrusion with wires coextruded in the wall of the plastic extrusion. Such a construction enables the extrusion to be flexible while maintaining its longitudinal rigidity. A problem with the use of a flexible, plastic tube-like section 13 is that plastics with a low flexural modulus typically have low tensile strength, causing the tube-like section 13 to stretch. With such an arrangement, when actuating control wire 18 opens end effector 14, the opening force may be lost in stretching tube-like section 13, transmitting less force to end effector 14. Therefore, to eliminate stretching of tube-like section 13 and maintain its flexibility, it is preferred to co-extrude wires into the walls of a plastic extrusion. For example, and as shown in FIGS. 10a–10c, tube-like section 13 includes a plastic extrusion 100 with a central hole 102 therethrough. Preferably, the outer diameter of extrusion 100 is approximately 0.095 inches and the inside diameter of extrusion 100 is approximately 0.055 inches. Extrusion 100 includes a plurality of metal wire 104 coextruded therein. As shown in FIGS. 10a–10c, extrusion 100 may include, for example, two to four wires 104 therein. Any suitable number of wires 104 coextruded in extrusion 100 to eliminate stretching of section 13 is within the scope of the present invention. Preferably, wires 104 have a diameter of approximately 0.010 inches. In addition, it is contemplated that either or both of axial sections 58 and 60 may be comprised of the configurations shown in FIGS. 10a–10c.

Control wire 18 is preferably flexible and longitudinally inelastic. Ideally, wire 18 is formed from 304 steel wire having an outer diameter of approximately 0.018 inches.

Deflecting wire 17 is preferably made of linearly elastic Nitinol, a nickel titanium alloy constituting about 49–51% nickel and 49–51% titanium. The linearly elastic properties of Nitinol are described in U.S. patent application Ser. No. 08/842,614 to Solar et al. entitled "Linearly Elastic Guide Wire", and commonly assigned. The complete disclosure of that patent application is hereby incorporated by reference. Deflecting wire 17 preferably has a diameter of 0.017 inch. It is important that wire 17 be an elastic material that is both flexible and has resilient properties. The material of wire 17 must be such that wire 17 can be deformed from its original state by an applied force and then return to that original state after that force is removed. As shown in FIG. 8, wire 17 is permanently bent prior to its insertion into coil 16 of bioptome 10. The permanent bend is located at a distance L from the distal end of wire 17. Length L is preferably approximately 0.75 inch and the angle of prebend is preferably approximately 30 degrees. It is to be understood that other lengths L and other angles of prebend are within the scope of this invention. During manufacture of bioptome 10, wire 17 is inserted into coil 16 and connected to proximal handle 12. Wire 17 is of a length so that once wire 17 is inserted into bioptome 10, wire 17 is fully contained within first axial portion 58 of bioptome 10. The stiffness of sleeve 15 and the elastic nature of wire 17 prevents the bend in wire 17 from assuming its prebend angle. Therefore, when wire 17 is fully contained within axial portion 58, wire 17 is substantially straight and does not cause axial portion 58 to bend.

As shown most clearly in FIG. 1, proximal handle 12 includes two actuators, a first actuator 62 connected to coil 16 and control wire 18 and a second actuator 64 connected to deflecting wire 17. Actuation of second actuator 64 causes deflecting wire 17 to deflect and/or rotate the distal end of bioptome 10 so that tangential biopsies may be taken. Actuation of first actuator 62 causes control wire 18 to actuate end effector 14 so that a tissue sample is taken.

Figure 2:
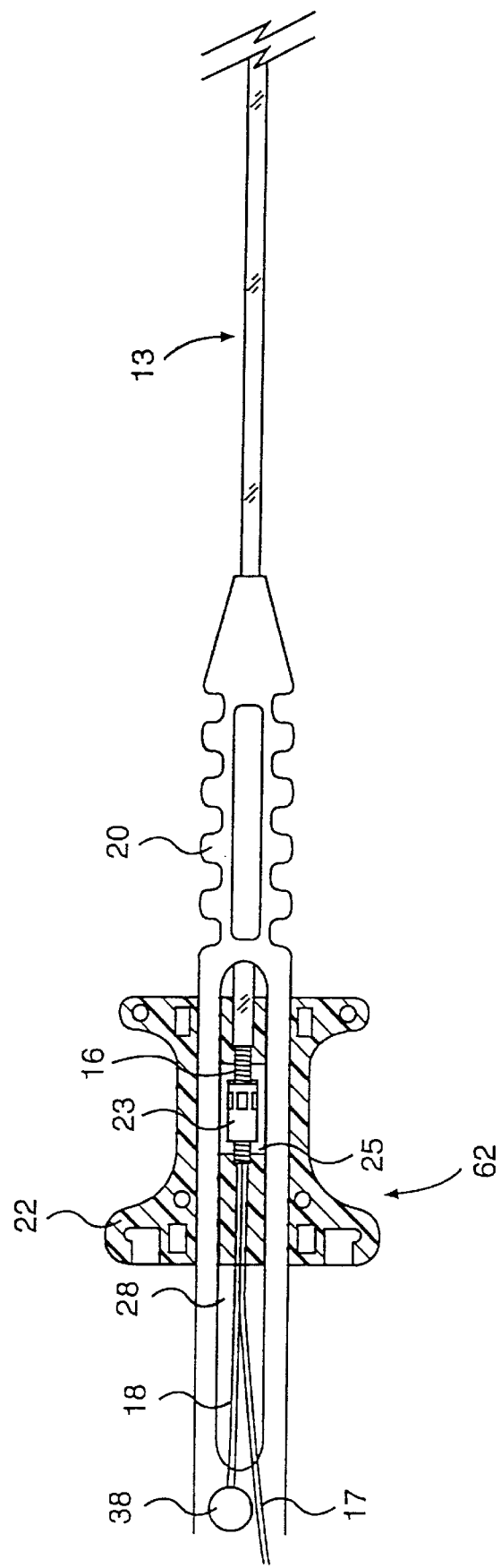
FIG. 2 is a sectional side elevation view of a portion of the proximal end of the bioptome shown in FIG. 1 according to a preferred embodiment of the present invention.

First actuator 62, shown in FIGS. 1 and 2, is similar to a conventional bioptome actuation device whose construction and operation are fully described in U.S. Pat. No. 5,645,075 to Palmer et al., the complete disclosure of which is incorporated herein by reference. First actuator 62 is modified from the Palmer et al. actuator is certain respects that will be described. For example, first actuator 62 is modified from the Palmer et al. actuation device to account for second actuator 64, which will be described herein. Similar to the Palmer et al. actuation device, first actuator 62 includes a central shaft 20 and an axially displaceable spool 22 surrounding shaft 20. A thumb ring 24 is provided near the proximal end of shaft 20 and slightly off-center from shaft 20. The distal end of shaft 20 includes a central longitudinal bore (not shown) through which section 13 containing coil 16 extends. A longitudinal slot 28 extends from the proximal end of bore 26 to a point slightly distal of thumb ring 24. A bore (not shown) and a set screw 38 are provided in shaft 20 just distal of thumb ring 24. The proximal end of control wire 18 passes through slot 28 and inserts into the bore where it is held by set screw 38.

Displaceable spool 22 includes structure so that the proximal end of coil 16 is fixed relative to spool 22. Spool 22 includes a central coil engaging member in the form of cylindrical recess 25 within spool 22. A crimp band 23 is secured to the proximal end of coil 16 and located within the cylindrical recess 25 so that coil 16 is fixed relative to spool 22 and moves axially with spool 22.

FIG. 1 shows second actuator 64 of proximal handle 12. Second actuator 64 includes a cylinder 66 that is axially slidable and rotatable within a longitudinal track 68. Deflecting wire 17 extends through slot 28 in shaft 20 to connect to cylinder 66. Wire 17 may be fixed to cylinder 66 in any suitable manner. For example, wire 17 may be fixed to cylinder 66 by a set screw in a similar manner as control wire 18 is fixed to handle 12. Axial displacement and rotation of cylinder 66 within track 68 respectively cause axial displacement and rotation of deflecting wire 17 within coil 16, resulting in the deflection and rotation of the distal end of bioptome 10 so that tangential biopsies may be taken.

Figure 4:
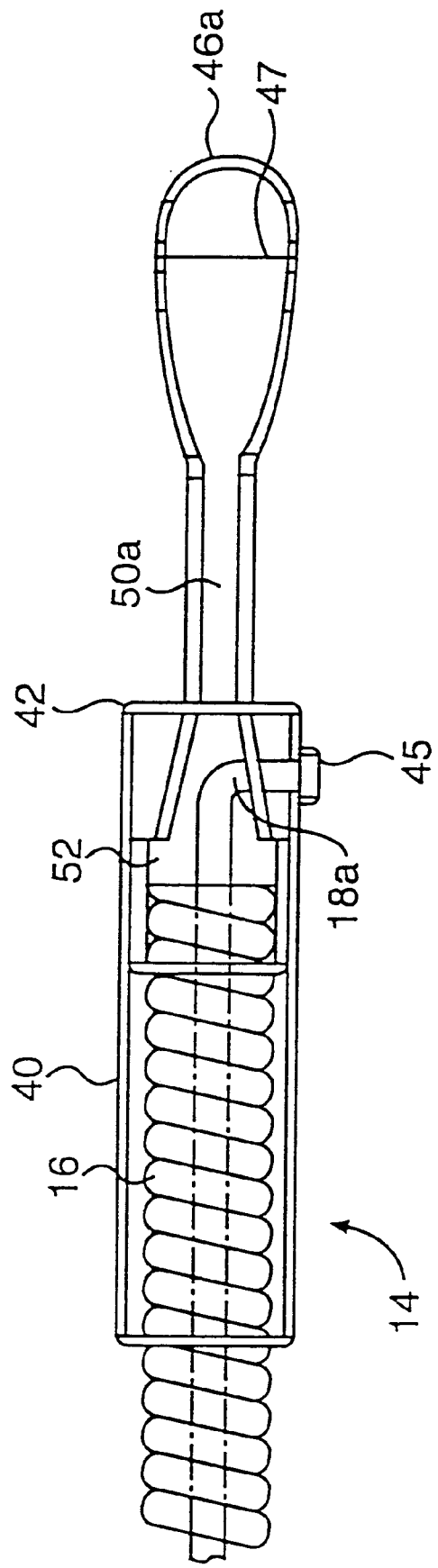
FIG. 4 is a top view in partial section of a portion of the distal end of the bioptome shown in FIG. 3 according to a preferred embodiment of the present invention.

FIGS. 3 and 4 show a side view and a top view of end effector 14 of bioptome 10. End effector 14 is a conventional end effector whose construction and operation are the same as that shown in U.S. Pat. No. 5,542,432 to Slater et al., the complete disclosure of which is incorporated by reference herein. It is to be understood that any conventional end effector assembly, including end effectors for clamping or cutting tissue or performing any other endoscopic surgical procedure, may be used with the inventive deflectable and rotatable distal assembly described herein. It is also to be understood that structure other than that described in the Slater et al. patent can be incorporated at the distal end to connect the end effector assembly to the remainder of the bioptome. Such alternative structure may be similar to that shown in U.S. Pat. No. 5,645,075 to Palmer et al., the complete disclosure of which is incorporated by reference herein. The end effectors shown and described in the Slater et al. and Palmer et al. patents are preferred uses for the deflectable and rotatable distal assembly and are illustrative only.

As shown in FIGS. 3 and 4, end effector 14 includes two main components: a jaw assembly 44 and a cylindrical sleeve 40. Sleeve 40 includes a distal edge 42. Jaw assembly 44 includes a pair of opposed jaw cups 46a, 46b each having a plurality of sharp teeth 48a, 48b. A resilient, preferably narrow arm 50a, 50b extends from each jaw cup 46a, 46b. Arms 50a, 50b and jaws 46a, 46b are preferably formed from a deep drawn piece of Nitinol.

A cylindrical base member 52 joins the proximal ends of arms 50a, 50b. Cylindrical base member 52 also couples to the distal end of flexible coil 16 by welding, soldering, crimping, or any other suitable manner. An alternative and preferred method of connecting arms 50a, 50b to each other and to coil 16 is disclosed in U.S. Pat. No. 5,645,075 to Palmer et al. As described more fully in the Palmer et al. patent, arms 50a and 50b may be connected to a threaded coupling or screw that is screwed into the distal end of coil 16.

In the embodiment shown in FIGS. 3–7, cylindrical sleeve 40 is coupled to the distal end of control wire 18 by a lateral hole in sleeve 40 which engages a bent end 18a of control wire 18. Bent end 18a is welded to hole 45 in the side of sleeve 40. Other methods of coupling control wire 18 to sleeve 40 are possible. Cylindrical sleeve 40 is slidably mounted over cylindrical base member 52 and is axially moveable over resilient arms 50a, 50b.

Figure 5:
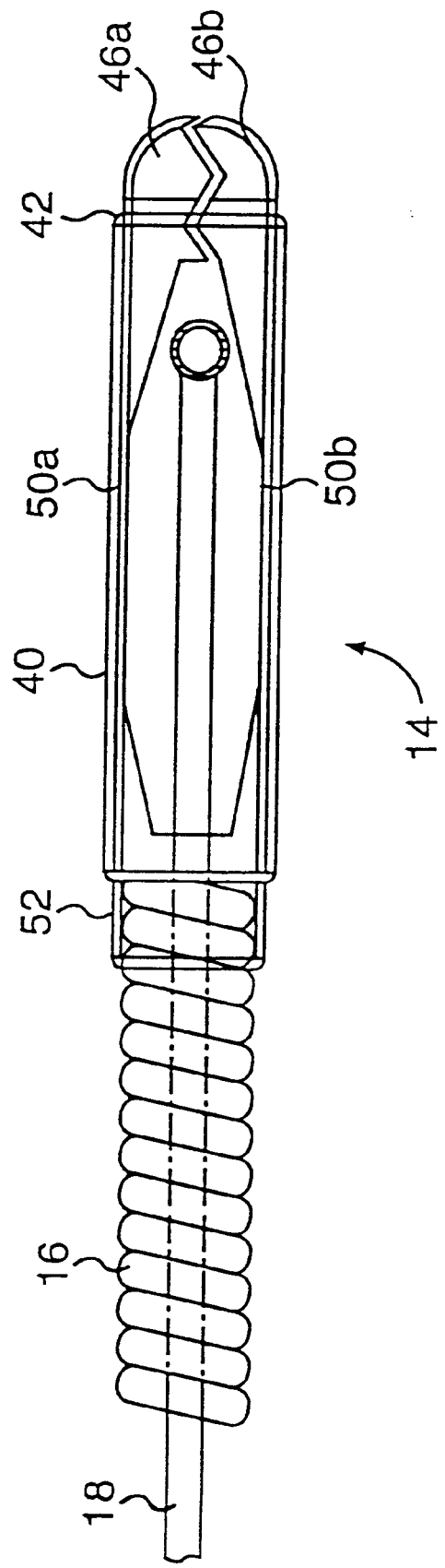
FIG. 5 is a side elevation view in partial section of a portion of the distal end of the bioptome shown in FIG. 3 with the end effectors closed according to a preferred embodiment of the present invention.

First actuator 62 connects to coil 16 to actuate end effector 14. Relative axial displacement of shaft 20 and spool 22 results in movement of coil 16 relative to control wire 18 and axial displacement of cylindrical sleeve 40 relative to jaw assembly 44. This results in the opening and closing of jaws 46a, 46b to take biopsy samples, as fully described in Slater et al. FIG. 5 shows jaws 46a, 46b closed upon relative axial displacement of shaft 20 and spool 22.

Figure 6:
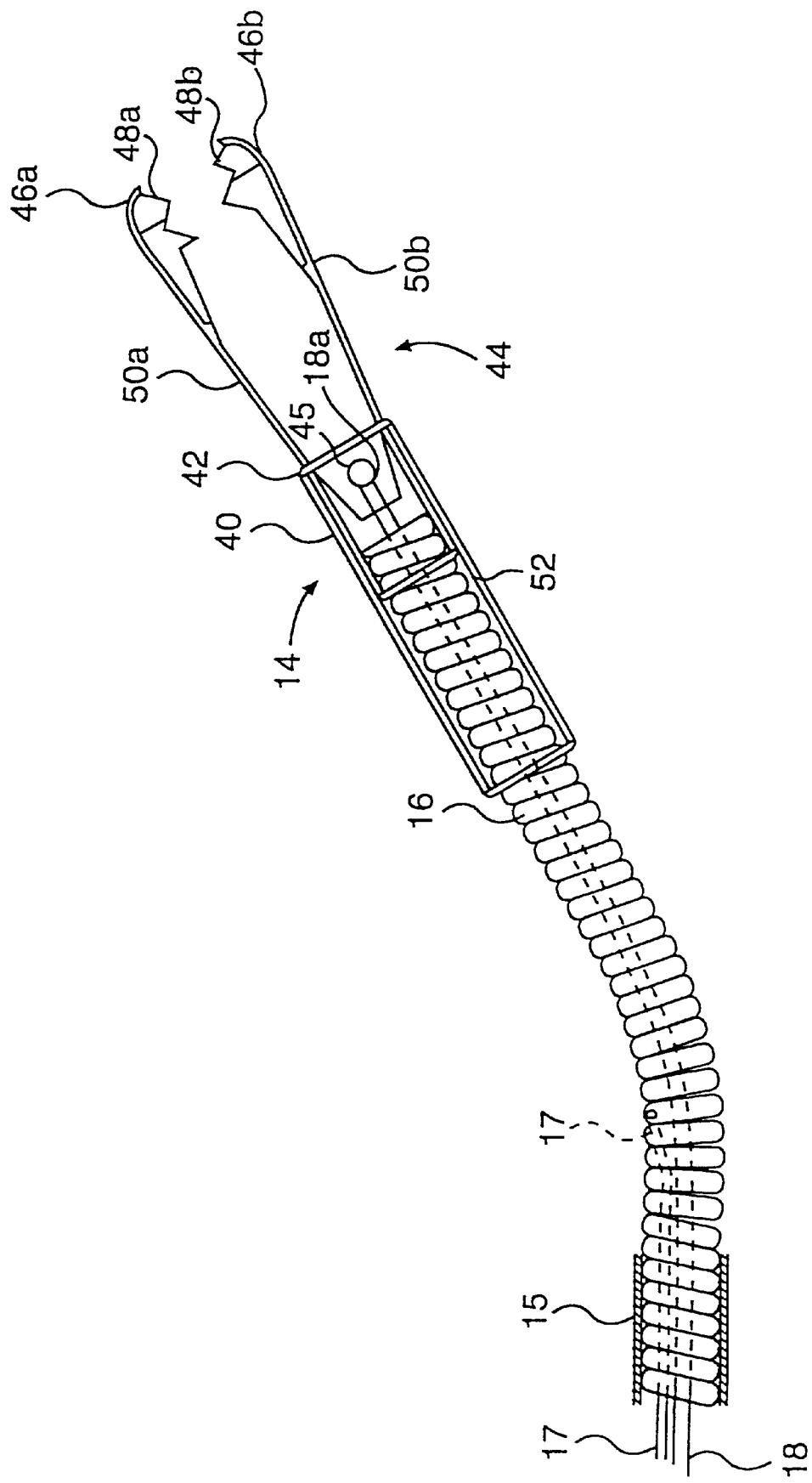
FIG. 6 is a side elevation view in partial section of the bioptome shown in FIG. 2 deflected at the distal end according to a preferred embodiment of the present invention.

As mentioned, actuation of second actuator 64 causes deflecting wire 17 to deflect and/or rotate the distal end of bioptome 10 so that tangential biopsies may be taken. FIG. 6 shows a deflected distal end of bioptome 10. Upon displacement of cylinder 66 in the distal direction, deflecting wire 17 advances axially within coil 16 and into second axial portion 60 of section 13, i.e. the portion not including sheath 15. Because second axial portion 60 is more flexible than first axial portion 58, deflecting wire 17 begins to assume its prebend angle of, for example, 30 degrees as wire 17 advances into second axial portion 60. Through a spring-like force, the return of the prebend of deflecting wire 17 deflects second axial portion 60 from its normally straight, axial position, allowing jaws 46a, 46b to reach biopsies lateral of end effector 14. Ideally, the amount of deflection of second axial portion 60 corresponds to the amount of axial displacement of deflecting wire 17 into second axial portion 60, i.e. second axial portion 60 deflects more as the axial displacement of deflecting wire 17 increases into second axial portion 60.

During endoscopic surgery, it also may be necessary to rotate the distal end of the bioptome, as well as deflect the distal end as just described, in order to reach and take certain tangential biopsies. Upon rotation of cylinder 66 within track 68, deflecting wire 17 rotates within coil 16. Rotation of deflecting wire 17, along with its axial advancement within coil 16, causes the deflection of second axial portion 60 at any point around the circumference of coil 16. In other words, rotation of deflecting wire 17 causes the distal end of the bioptome to assume any desired position of angular orientation. For example, FIG. 7 shows a distal end of bioptome 10 deflected from its normally straight position and 180° from the deflected position shown in FIG. 6.

It will be apparent to those skilled in the art that various modifications and variations can be made in the endoscopic bioptome having a deflectable and rotatable distal end of the present invention and in construction of this bioptome without departing from the scope or spirit of the invention. As an example, other handle and actuation assemblies may be used to operate the end effector and deflecting device. As a further example, means other than a sheath can be used for obtaining a relative difference in flexibility between the first and second axial portions. Such means may include use of a different, more flexible coil material for the portion of coil within second axial portion 60.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoscopic bioptome having a proximal end and a distal end, the bioptome comprising:

a proximal handle assembly including first and second actuators;

a distal end effector assembly having jaws for cutting tissue samples;

a hollow member extending between the handle and the end effector assembly, the hollow member including a first axial portion extending from the proximal end to a second axial portion at the distal end of the hollow member, the second axial portion being more flexible than the first axial portion;

a control member connected at the proximal end to the handle assembly and at the distal end to the end effector assembly, wherein actuation of the first actuator causes the control member to open and close the jaws; and a deflecting device connected at the proximal end to the second actuator and extending through at least a portion of the hollow member, wherein actuation of the second actuator causes the deflecting device to axially displace into the second axial portion to deflect the distal end of the hollow member.

2. The endoscopic bioptome according to claim 1, wherein the hollow member includes a coil surrounded by an outer sleeve along the first axial portion.

3. The endoscopic bioptome according to claim 1, wherein the hollow member is comprised of an extrusion having at least one wire coextruded into the extrusion.

4. The endoscopic bioptome according to claim 1, wherein the amount of deflection of the distal end of the hollow member corresponds to the amount of axial displacement of the deflecting device into the second axial portion.

5. The endoscopic bioptome according to claim 1, wherein actuation of the second actuator causes the deflecting device to rotate.

6. The endoscopic bioptome according to claim 5, wherein rotation of the deflecting device causes the distal end of the hollow member to deflect to a predetermined angular orientation.

7. The endoscopic bioptome according to claim 1, wherein the deflecting device includes a distal end section that remains straight when the distal end section is within the first axial portion of the hollow member and bends when the distal end section is within the second axial portion of the hollow member.

8. The endoscopic bioptome according to claim 7, wherein the distal end section of the deflecting device assumes a bend of approximately 30 degrees when the distal end section is within the second axial portion of the hollow member.

9. The endoscopic bioptome according to claim 8, wherein the bend in the deflecting device is at a distance of approximately 0.75 inch from an end of the deflecting device.

10. The endoscopic bioptome according to claim 1, wherein the deflecting device is a wire.

11. The endoscopic bioptome according to claim 10, wherein the wire is comprised of an elastic material having resilient properties.

12. The endoscopic bioptome according to claim 1, wherein the hollow member includes a metal coil.

13. The endoscopic bioptome according to claim 12, wherein the coil includes a prestretched portion corresponding to the second axial portion of the hollow member.

14. An endoscopic surgical instrument having a proximal end and a distal end, the instrument comprising:

a proximal manual actuator including first and second actuators;

a distal end effector assembly for performing a surgical operation;

a hollow member extending between the manual actuator and the end effector assembly, the hollow member including a first axial portion extending from the proximal end to a second axial portion at the distal end of the flexible member, the second axial portion being more flexible then the first axial portion;

a control member connected at the proximal end to the manual actuator and at the distal end to the end effector assembly so that actuation of the first actuator causes the distal end effector to perform the surgical operation; and a deflecting device connected at the proximal end to the second actuator and extending along the flexible member, wherein actuation of the second actuator causes the deflecting device to axially displace into the second axial portion to deflect the distal end of the flexible member.

15. An endoscopic bioptome having a proximal end and a distal end, the bioptome comprising:

a proximal handle assembly including at least one actuator;

a distal end effector assembly having jaws for cutting tissue samples;

a hollow member extending between the handle and the end effector assembly, the hollow member including a first axial portion extending substantially the entire length of the hollow member from the proximal end and a second axial portion at the distal end of the hollow member;

a control member extending through the hollow member and connected at the proximal end to the handle and at the distal end to the end effector assembly, wherein actuation of the at least one actuator causes the control member to open and close the jaws; and a deflecting device connected at the proximal end to the at least one actuator and extending through the first axial portion of the hollow member, wherein the first axial portion has a first stiffness so that a distal end of the deflecting device remains substantially straight when the distal end of the deflecting device is contained within the first axial portion, and the second axial portion has a second stiffness so that the distal end of the deflecting device bends when the distal end of the deflecting device is contained within the second axial portion.

16. The endoscopic bioptome according to claim 15, wherein the hollow member includes a coil surrounded by an outer sleeve along the length of the coil corresponding to the first axial portion.

17. The endoscopic bioptome according to claim 16, wherein a distal end of the outer sleeve terminates at a proximal end of the second axial portion.

18. The endoscopic bioptome according to claim 17, wherein actuation of the at least one actuator axially displaces the deflecting device distally into the portion of the coil corresponding to the second axial portion to deflect the portion of the coil corresponding to the second axial portion.

19. The endoscopic bioptome according to claim 15, wherein actuation of the at least one actuator causes the deflecting device to axially displace towards the distal end.

20. The endoscopic bioptome according to claim 19, wherein the amount of deflection of the distal end of the hollow member corresponds to the amount of axial displacement of the deflecting device into the second axial portion.

21. The endoscopic bioptome according to claim 15, wherein actuation of the at least one actuator causes the deflecting device to rotate.

22. The endoscopic bioptome according to claim 21, wherein rotation of the deflecting device causes the distal end of the hollow member to deflect to a predetermined angular orientation.

23. The endoscopic bioptome according to claim 15, wherein the distal end of the deflecting device assumes a bend of approximately 30 degrees when the distal end of the deflecting device is within the second axial portion of the hollow member.

24. The endoscopic bioptome according to claim 23, wherein the bend in the deflecting device is at a distance of approximately 0.75 inch from an end of the deflecting device.

25. The endoscopic bioptome according to claim 15, wherein the deflecting device is a wire.

26. The endoscopic bioptome according to claim 25, wherein the wire is comprised of an elastic material having resilient properties.

* * * * *